United States Patent [19]

Osburn

[11] Patent Number: 4,496,357

[45] Date of Patent: Jan. 29, 1985

[54] SKIN BARRIER COMPOSITION

[75] Inventor: Frank G. Osburn, Hanover Park, Ill.

[73] Assignee: Hollister Incorporated, Libertyville, Ill.

[21] Appl. No.: 272,192

[22] Filed: Jun. 10, 1981

[51] Int. Cl.$^3$ .......................... A61F 5/44; B01J 13/00
[52] U.S. Cl. ................................ 604/336; 252/315.1; 252/315.6; 128/156
[58] Field of Search ................. 252/316, 315.1, 315.6; 128/283, 156; 604/336

[56] References Cited

U.S. PATENT DOCUMENTS

| | | | |
|---|---|---|---|
| 3,339,546 | 9/1967 | Chen | 128/156 |
| 3,980,084 | 9/1976 | Kross . | |
| 4,071,374 | 1/1978 | Minton | 252/316 X |
| 4,100,093 | 7/1978 | Rialdi | 252/315.6 |
| 4,152,272 | 5/1979 | Young | 252/8.5 |
| 4,191,677 | 3/1980 | Strand | 260/37 EP |
| 4,253,460 | 3/1981 | Chen | 128/283 |
| 4,254,008 | 3/1981 | Krsek . | |
| 4,350,785 | 9/1982 | Habib | 604/336 X |
| 4,356,819 | 11/1982 | Potaczek | 128/156 |
| 4,359,047 | 11/1982 | Potaczek | 128/156 |

OTHER PUBLICATIONS

Grace, Davison Chemical Division, "Davison Family of Syloid® Silicas at Work", Mar. 1975.

*Primary Examiner*—Richard D. Lovering
*Assistant Examiner*—Catherine S. Kilby

[57] ABSTRACT

A skin barrier composition is provided which is moisture-absorbing while being resistant to urine and other body fluids and substantially non-swelling. It is composed of a continuous elastomer phase containing particulate hydrocolloid together with fumed silica. The hydrocolloid provides the water-absorbency while the fumed silica controls the swelling. The composition is adapted for ostomy and wound drainage applications, and has especially desirable properties for urostomy and ileostomy use where corrosive drainage is encountered.

8 Claims, No Drawings

SKIN BARRIER COMPOSITION

BACKGROUND AND PRIOR ART

The general field of this invention relates to skin barriers for ostomy or wound drainage use. For this purpose, the compositions are prepared in the form of rings, sheets or blankets, which are fitted around the stoma ostomy opening protecting the skin from the intestinal fluids (ileostomy and colostomy) or urine (urostomy). Ostomy appliances for collecting the discharged fluids may be applied to the outer surface of the skin barriers. To facilitate this attachment, the outer surfaces of the barriers may comprise porous or nonporous films which are laminated to the sheet of the barrier composition, and which usually have their outer surface coated with a pressure-sensitive adhesive, depending on the adhesive properties of the material itself. The present invention is not concerned with such structural details but only with the barrier composition, and particularly with barrier compositions adapted for urostomy and ileostomy use. Ostomy barrier compositions composed of mixtures of elastomers with hydrocolloids are known. See, for example, U.S. Pat. Nos. 3,339,546 and 4,253,460. For this type of barrier composition, the elastomer, which may be a natural or synthetic rubber, or mixtures of such rubber, comprises the continuous phase, and the hydrocolloid is dispersed therein in particulate form. Both natural hydrocolloid gums such as pectin and gelatin and synthetic hydrocolloids such as carboxymethylcellulose have been used in various admixtures. The rubber such as polyisobutylene provides the compositions with an adhesive, dry tack characteristic. The dispersed particles of hydrocolloid absorb water, and also when wet acquire a wet tack adhesive characteristic. Such compositions have been formulated in a wide range of proportions of elastomer to hydrocolloid for use with intestinal ostomies, such as ileostomies and colostomies, and 35 to 45% hydrocolloid. For urostomy use, larger proportions of the elastomer are used, such as 85 to 95% polyisobutylene.

In urostomy applications, the barrier composition is subject to attack by the urine which is discharged through the stoma. At the same time, however, the inner surface of the barrier is in contact with the skin and desirably absorbs the moisture discharged from the skin as perspiration. It is desirable to provide the barrier composition with a moisture absorbing characteristic. However, the inclusion of hydrocolloid which provides the moisture-absorbing characteristic also makes the composition urine-absorbing. The absorbed urine tends to attack and degrade the composition. Further, if too much moisture or urine is absorbed, the hydrocolloid swells undesirably, causing the barrier to pucker and pull away from the skin. This condition can progress until the barrier becomes unusable and must be replaced. For uses such as urostomy and ileostomy, extended mechanical and adhesive endurance of the barrier is important. It may be desired to leave the barrier in place for a week or longer. Therefore, the art has been presented with a difficult problem of formulating barrier compositions of optimum characteristics for urostomy use. Heretofore, no such composition has been provided which is moisture-absorbing while substantially non-swelling, and at the same time provides a high level of resistance to urine and other corrosive fluids such as found with ileostomies.

SUMMARY OF INVENTION

This invention is based on the discovery that the properties of elastomeric skin barriers can be greatly improved for urostomy use by dispersing fumed silica in the elastomer together with hydrocolloid. By limiting the amount of hydrocolloid employed to a level sufficient to provide the desired water absorbency, the swelling of the composition may be limited to a negligible amount and the corrosive fluid resistance of the composition substantially improved by incorporating a few percent of fumed silica. The mechanism by which these results are accomplished is not fully understood. However, if the amount and character of the hydrocolloid employed provides too high a degree of water absorbency, the composition will swell despite the presence of the fumed silica. Therefore, both the hydrocolloid and the fumed silica must be employed within specified ranges if a composition is to be obtained which is water absorbing while having minimal swelling. The required relative proportions will be described in the following detailed description. Prior to the present invention, fumed silica has only been used in a different kind of barrier composition. For many years, hydrocolloid gums, such as karaya, have been mixed with glycerin or other polyhydroxy alcohol to produce a mixture which will gel to a solid and can be formed during gelation into sheets or rings. Recently, such sheets and rings containing a few percent of fumed silica have been introduced for commercial use in the United States by the assignee of the present application, Hollister Incorporated, Chicago, Ill. The gelled hydrocolloid compositions containing the fumed silica are more resistant to degradation by intestinal fluids and/or urine.

DETAILED DESCRIPTION

The compositions of the present invention are composed principally of one or more elastomers. As described in U.S. Pat. Nos. 3,339,546 and 4,253,460, natural or synthetic rubbers may be used, or mixtures thereof. Polyisobutylene, or mixtures of polyisobutylene with butyl rubber are particularly desirable. Butyl rubber is a copolymer of isobutylene with a minor amount of isoprene, and has a high average molecular weight than polyisobutylene. Other rubbers which can be used include natural rubber, silicone rubber, acrylonitrile rubber, polyurethane rubber, styrene/isobutylene/styrene rubber, ethylene/propylene rubber, and ethylene/propylene/diamine rubber.

In the compositions, the elastomer provides the continuous phase, and the particulate hydrocolloid and fumed silica are dispersed therein. In general, on a weight percent basis, the compositions should be formulated so that they contain from 50 to 90% elastomer, from 10 to 35% hydrocolloid, and from 1 to 10% fumed silica. Preferably, at least 3 parts by weight of the elastomer are present per part of the hydrocolloid. The hydrocolloid is preferably a natural hydrocolloid gum, or mixture of such gums, such as gelatin, pectin, guar, ghatti, karaya, xanthan and locust bean. Synthetic hydrocolloids such as sodium carboxymethylcellulose can be used but are less desirable. One particularly desirable combination of hydrocolloids is a mixture of gelatin and pectin. The hydrocolloids are used in the form of powders which are dry to the touch, but which will contain some moisture internally. In other words, the natural hydrocolloid gums are used in their standard commercial form.

The fumed silica is also used in its standard commercial form, which comprises the ultrafine particles produced by flame hydrolysis of silicon tetrachloride. Such fumed silica can be obtained from various manufacturers, including the "Cab-O-Sil" products of Cabot Corporation, Boston, Mass., and the "Aerosil" products of Degussa, Inc., New York, N.Y. These products are silicon dioxide in colloidal form having very high surface areas. For example, one suitable specific product is the grade M-5 of "Cab-O-Sil". The amount of fumed silica employed in the composition should be sufficient to substantially inhibit their swelling although sufficient hydrocolloid is present to make the compositions moisture-absorbing. Weight percentages in the range of 2 to 8%, such as 4 to 6%, are particularly desirable.

A preferred general formula for the novel urostomy skin barrier compositions of the present invention is as follows:

| Preferred Formula | |
|---|---|
| Ingredients | Wt. % |
| Polyisobutylene | 70 to 85 |
| Natural hydrocolloid gum | 10 to 25 |
| Fumed silica | 1 to 10 |

As indicated by the foregoing formula, the polyisobutylene or other elastomer comprises at least 70% by weight of a composition while the natural hydrocolloid gum, or mixture of hydrocolloid gums comprises a maximum of 25% of the composition. Preferably, at least 15 weight percent of the hydrocolloid gum is used (viz. 15 to 25%) in admixture with from 2 to 8% of the fumed silica.

The manufacturing of the compositions of this inventions can be carried out in a known matter, such as the procedures described in U.S. Pat. Nos. 3,339,546 and 4,253,460. Roll mixers or blade mixers can be used to blend the hydrocolloid powders and the fumed silica into the elastomer, the mixing being continued until a uniform dispersion is obtained.

The present invention and the improved results obtainable thereby are further illustrated by the following examples.

EXAMPLE I

The presently preferred embodiment of the present invention is set out below as Formula A:

| Formula A | |
|---|---|
| Ingredients | Wt. % |
| Polyisobutylene | 75.0 |
| Fumed Silica | 5.0 |
| Gelatin | 12.0 |
| Pectin | 8.0 |

The polyisobutylene may be obtained from Exxon Chemical Co., Elastomer Dept., Houston, Tex., as "Vistanex" grade LM-MH, or grade LM-MS, or the "Opanol" products (B-10 to B-18) of BASF Wyandotte Corp., Holland, Mich. Such polyisobutylenes have a viscosity average molecular weight within the range from 36,000 to 58,000 (Flory). The fumed silica may be "Cab-O-Sil M-5" Cabot Corporation, Boston, Mass. The gelatin and pectin can be obtained from various commercial sources, and are in the form of fine powders.

The ingredients of Formula A can be combined according to the following procedure; Conventional blending and mixing equipment can be employed, such as banbary mixers, roll mill mixers, sigma blade or cam-blade mixers, or multiple screw extruders. The blending and mixing is normally accomplished with no heat input, although heat may be added if required to promote the mixing. The mixing speed is set at a rate fast enough to be efficient, but slow enough to prevent excessive amounts of the powder ingredients from being blown out of the mixer. The polyisobutylene or other elastomeric polymer is added to the mixer, which is run for one to three minutes to distribute the elastomer throughout the mixing chamber. The powder ingredients (fumed silica, gelatin, and pectin, or other hydrocolloids in powder form) are added slowly, either one at a time or simultaneously. Following the powder addition, the mixing is continued for several more minutes, preferably for five to ten minutes, to insure full wetting and dispersion of the powders. After complete dispersion is obtained, the mixing is preferably terminated, since over-mixing may increase the amount of entrapped air. The composition may be formed into sheets or thin blankets or into rings by standard procedures.

EXAMPLE II

The composition of Formula A was subjected to an endurance test and a swelling test. The procedures used were as follows:

Endurance Test

For the endurance test, a simulated urine was prepared as described in *Remington's Pharmaceutical Sciences,* "Urine", pg. 598-9, Ed 15 (1975).

The endurance test apparatus includes a tank for containing the simulated urine, and a plurality of tripod testing fixtures, which may be placed in the tank in contact with the solution. The testing fixture has a platform at the top with a sample-receiving recess. The center portion of the recess is cut-out to provide an opening through the platform. When placed in test position, the test samples bridge the openings. U-shaped weights are then placed over the samples. These weights are in the form of steel hooks weighing approximately 7.4 grams. In use, the hooks are placed over the samples so that when the hooks break through the samples they would fall freely through the openings in the platforms. Nylon strings are attached to the upper cross-arm portions of the inverted U-shaped hooks and the strings are attached to the operating levers of micro switches, the lengths of strings being selected so that when the sample is broken, the micro switch will be activated, and a timing clock for the particular sample will be stopped. In starting the test, after the samples have been placed in the tank and the strings attached to the microswitch levers, the simulated urine is added to the tanks to a level above the position of the samples, and the timing clocks for each sample are started. The elapsed time for breakthrough of each sample is thereby automatically recorded.

The samples for the endurance test were die cut using a steel rule die to a size of 28×10×1.5 mm. The center portions of the samples were engaged by the weighted hooks. The measured time for breakthrough was corrected by multiplying the measured time by 1.0 grams of the sample divided by actual weight of the sample.

Swelling Test

In preparing the test apparatus, a measuring device, in millimeters, such as part of a paper or plastic ruler, is cut to fit on the underneath side of the bottom of a 9 cm. diameter petri dish. A line is scribed across the width of the measuring device 3 cm. in from one side. The scribed measuring device is affixed to the bottom underneath side of the petri dish so that the graduations and scribed mark can be easily read through the petri dish when full of fluid. Pellets of the sample material approximately 28×10×1.5 mm. in size are cut for the test. Each test pellet is affixed to the floor of the petri dish so that the leading edge of the short side touches the scribe mark, andthe longitudinal edge, the ruler's running line. The petri dish is filled with simulated urin, prepared as described above, (or other test solution) and covered. After a period of 72 hours, the amount of swell on each edge is determined and reported.

Transverse Swell (width) equals:

$$\frac{\text{amount one edge} + \text{amount second edge}}{2}$$

Longitudinal Swell (length) equals:

$$\frac{\text{amount one edge} + \text{amount second edge}}{2}$$

The test results are reported below in Tables A and B.

TABLE A

Endurance to Simulated Urine

| Description of Samples | Endurance Time (hrs.)[a] |
|---|---|
| Formula A with porous backing on one side | 194 |
| Product I (Commercial ostomy skin barrier with porous backing on one side)[b] | 35 |
| Product II (Commercial ostomy skin barrier with impervious backing on one side)[c] | 26 |
| Product III (Commercial ostomy skin barrier with impervious backing on one side)[d] | 107 |

[a] Averages of multiple runs.
[b] Composed of a mixture of polyisobutylene and hydrocolloid powder (no silica).
[c] Same as [b] but from a different manufacturer.
[d] Same as [b] and [c] but from a different manufacturer.

TABLE B

Swelling to Simulated Urine

| Description of Samples | Swell Level (mm)[a] Longitudinal | Transverse |
|---|---|---|
| Formula A with porous backing on one side | 1.0 | 1.0 |
| Product I[b] | 10.0 | 10.0 |
| Product II[c] | 8.0 | 7.0 |
| Product III[d] | None[e] | None[e] |

[a] Averages of multiple runs.
[b] [c] and [d] Same as Table A.
[e] Product swelling was negligible indicating that water absorption was also very small.

The present invention can be practiced in other embodiments. For example, the continuous elastomer phase can contain a polymer or copolymer of a kind used to modify the vicosity and flow properties of elastomers. Such polymers include polyethylene, such as low density polyethylene, polyvinyl acetate, and ethylene/vinyl acetate copolymers. Such polymers preferably provide only a minor proportion by weight of the elastomer phase, for example, being present in amounts of from 10 to 90 parts by weight per 100 parts of the elastomer. In another variation of the formula set forth herein, a water-absorbing synthetic polymer can be substituted for the presently preferred natural hydrocolloid gum. For example, such water-absorbing polymers include polyvinyl alcohols and polyanhydrides.

The foregoing compositions may be formed into sheets by passing the material through a calender having a pre-set gap, or the sheets may be formed by compression in a mold cavity of the desired depth. The compositions may also be formed by passing the mixed material through conventional extrusion equipment equipped with a slot or tape die set to extrude a ribbon of approximately the desired thickness. If necessary the extruded ribbon can be further compressed in thickness by passing it through one or more sets of compression rollers. The currently preferred mode of preparation consists of extruding a ribbon of the desired width and thickness directly onto release paper, which is then cut into stock "preforms". If desired, the preforms can be covered, on their exposed sides, with one of several types of backings, either porous or non-porous films being used. Among the available backings, it is preferable to use a plastic film, porous or non-porous, with or without a contact adhesive; non-woven as well as woven fabrics; porous or non-porous types of contact adhesive backed tapes. The backings may be applied by hand or in conjunction with the compression rollers referred to above.

I claim:

1. A skin barrier composition in the form of integral rings or blankets for application around a stoma composed substantially entirely of a continuous polyisobutylene phase having dispersed therein particulate hydrocolloid together with fumed silica, said composition containing on a weight percent basis from 50 to 90% of the polyisobutylene phase, from 10 to 35% hydrocolloid, and from 1 to 10% fumed silica, at least 3 parts by weight of said polyisobutylene phase being present per part of said hydrocolloid.

2. The composition of claim 1 in which said hydrocolloid consists of one or more natural hydrocolloid gums.

3. The compositions of claim 1 or claim 2 in which said compositions contained from 2 to 8% by weight of fumed silica.

4. A skin barrier composition in the form of integral rings or blankets for application around a stoma composed substantially entirely of a continuous polyisobutylene phase having dispersed therein particulate hydrocolloid together with fumed silica, said composition containing on a weight percent basis from 70 to 85% of the polyisobutylene phase, from 10 to 25% hydrocolloid, and from 1 to 10% fumed silica.

5. A skin barrier composition in the form of integral rings or blankets for application around a stoma composed substantially entirely of a continuous polyisobutylene phase having dispersed therein particulate hydrocolloid together with fumed silica, said composition containing on a weight percent basis from 70 to 85% of the polyisobutylene phase, from 10 to 25% hydrocolloid, and from 2 to 8% fumed silica.

6. A skin barrier composition in the form of integral rings or blankets for application around a stoma composed substantially entirely of a continuous polyisobutylene phase having dispersed therein particulate natural hydrocolloid gum together with fumed silica, said composition containing on a weight percent basis from 70 to 85% of polyisobutylene, from 15 to 25% of natural hydrocolloid gum, and from 2 to 8% of fumed silica.

7. The composition of claim 6 in which said natural hydrocolloid gum is selected from the class consisting of gelatin, pectin, guar, ghatti, karaya, and xanthan, and mixtures thereof.

8. A skin barrier composition in the form of integral rings or blankets for application around a stoma composed substantially entirely of a continuous polyisobutylene phase having dispersed therein particulate gelatin and pectin together with fumed silica, said composition containing approximately on a weight percent basis 75% polyisobutylene, 12% gelatin, 8% pectin, and 5% fumed silica.

* * * * *